(12) United States Patent
Esfandiari

(10) Patent No.: US 7,387,890 B2
(45) Date of Patent: Jun. 17, 2008

(54) IMMUNOASSAY DEVICES AND USE THEREOF

(75) Inventor: Javanbakhsh Esfandiari, Stoney Brook, NY (US)

(73) Assignee: Chembio Diagnostic Systems, Inc., Medford, NY (US)

( * ) Notice: Subject to any disclaimer, the term of this patent is extended or adjusted under 35 U.S.C. 154(b) by 382 days.

(21) Appl. No.: 11/014,140

(22) Filed: Dec. 16, 2004

(65) Prior Publication Data

US 2006/0134803 A1    Jun. 22, 2006

(51) Int. Cl.
*C12M 1/34*    (2006.01)

(52) U.S. Cl. .................. 435/287.2; 422/56; 422/57; 422/58; 435/5; 435/287.1; 435/287.7; 435/288.4; 435/805; 435/810; 435/970; 436/514; 436/805; 436/810

(58) Field of Classification Search .................. 422/56, 422/57, 58; 435/5, 287.1, 287.2, 287.7, 288.4, 435/805, 810, 970; 436/514, 805, 810
See application file for complete search history.

(56) References Cited

U.S. PATENT DOCUMENTS

| | | | |
|---|---|---|---|
| 3,960,488 A | 6/1976 | Giaever | |
| 4,235,601 A | 11/1980 | Deutsch et al. | |
| 4,740,468 A | 4/1988 | Weng et al. | |
| 4,826,759 A | 5/1989 | Guire et al. | |
| 4,857,453 A | 8/1989 | Ullman et al. | |
| 4,870,003 A | 9/1989 | Kortright et al. | |
| 4,886,742 A | 12/1989 | Kortright et al. | |
| 4,956,275 A | 9/1990 | Zuk et al. | |
| 4,960,691 A | 10/1990 | Gordon et al. | |
| 4,981,786 A | 1/1991 | Dafforn et al. | |
| 5,137,808 A | 8/1992 | Ullman et al. | |
| 5,147,780 A | 9/1992 | Pouletty et al. | |
| 5,160,701 A * | 11/1992 | Brown et al. .................. 422/56 |
| 5,169,789 A | 12/1992 | Bernstein | |
| 5,296,192 A | 3/1994 | Carroll et al. | |
| 5,306,623 A | 4/1994 | Kiser et al. | |
| 5,391,478 A | 2/1995 | Greene et al. | |
| 5,418,136 A | 5/1995 | Miller et al. | |
| 5,418,142 A | 5/1995 | Kiser et al. | |
| 5,468,648 A | 11/1995 | Chandler | |
| 5,482,830 A | 1/1996 | Bogart et al. | |

(Continued)

FOREIGN PATENT DOCUMENTS

WO    WO 88/08534    11/1988

*Primary Examiner*—Christopher L. Chin
(74) *Attorney, Agent, or Firm*—Gordon & Jacobson, PC

(57) ABSTRACT

An immunoassay device has a housing defining a first opening for receiving a solution and a second opening through which a liquid sample is deposited, a strip of sorbent material having a test site with immobilized antigen or antibody for the ligand to be tested, and a filter for filtering the sample. The filter is located at the second opening and directly above the test site. The sorbent material defines a horizontal flow path in the housing for the solution from the first opening to the test site. In use, the sample is first applied via the filter to the test site, and then, after the ligand has been captured, a buffer added through the first opening is used to cause a secondary specific binder conjugated to a marker to migrate horizontally by capillary action to the test site where it can bind to the already captured ligand. This immunoassay offer several advantages over the traditional chromatographic immunoassays.

19 Claims, 3 Drawing Sheets

U.S. PATENT DOCUMENTS

| | | | |
|---|---|---|---|
| 5,500,350 A | 3/1996 | Baker et al. | |
| 5,541,057 A | 7/1996 | Bogart et al. | |
| 5,550,063 A | 8/1996 | Bogart | |
| 5,552,272 A | 9/1996 | Bogart | |
| 5,559,041 A | 9/1996 | Kang et al. | |
| 5,591,645 A | 1/1997 | Rosenstein | |
| 5,607,863 A | 3/1997 | Chandler | |
| 5,629,164 A | 5/1997 | Rivers | |
| 5,629,214 A | 5/1997 | Crosby | |
| 5,639,671 A | 6/1997 | Bogart et al. | |
| 5,641,639 A | 6/1997 | Perry | |
| 5,658,801 A * | 8/1997 | Poissant et al. | 436/518 |
| 5,714,389 A | 2/1998 | Charlton et al. | |
| 5,723,345 A | 3/1998 | Yamauchi et al. | |
| 5,726,010 A | 3/1998 | Clark | |
| 5,728,587 A | 3/1998 | Kang et al. | |
| 5,750,333 A | 5/1998 | Clark | |
| 5,821,073 A * | 10/1998 | Lee | 435/7.92 |
| 5,824,268 A | 10/1998 | Bernstein et al. | |
| 5,846,838 A | 12/1998 | Chandler | |
| 5,869,272 A | 2/1999 | Bogart et al. | |
| 5,869,345 A | 2/1999 | Chandler | |
| 5,877,028 A | 3/1999 | Chandler et al. | |
| 5,879,951 A | 3/1999 | Sy | |
| 5,948,695 A | 9/1999 | Douglas et al. | |
| 5,955,377 A | 9/1999 | Maul et al. | |
| 5,989,921 A | 11/1999 | Charlton et al. | |
| 5,998,220 A | 12/1999 | Chandler | |
| 6,017,767 A | 1/2000 | Chandler | |
| 6,030,770 A | 2/2000 | Brust | |
| 6,040,195 A | 3/2000 | Carroll et al. | |
| 6,087,184 A | 7/2000 | Magginetti et al. | |
| 6,106,732 A | 8/2000 | Johnston et al. | |
| 6,168,956 B1 | 1/2001 | Chandler | |
| 6,284,550 B1 | 9/2001 | Carroll et al. | |
| 6,436,722 B1 | 8/2002 | Clark et al. | |
| 6,485,982 B1 | 11/2002 | Charlton | |
| 6,489,129 B1 | 12/2002 | Faatz et al. | |
| 6,528,321 B1 | 3/2003 | Fitzgerald et al. | |
| 6,548,309 B1 | 4/2003 | Moore et al. | |
| 6,617,116 B2 | 9/2003 | Guan et al. | |
| 6,645,732 B2 | 11/2003 | Faatz et al. | |
| RE38,430 E | 2/2004 | Rosenstein | |
| 6,699,722 B2 | 3/2004 | Bauer et al. | |
| 6,727,073 B1 | 4/2004 | Moore et al. | |
| 6,737,277 B1 | 5/2004 | Kang et al. | |
| 6,780,651 B2 | 8/2004 | Douglas et al. | |
| 6,824,997 B1 | 11/2004 | Moore et al. | |
| 2002/0058330 A1 | 5/2002 | Carroll et al. | |
| 2003/0045001 A1 | 3/2003 | Burgess et al. | |
| 2004/0248322 A1 | 12/2004 | Charlton | |

* cited by examiner

IMMUNOASSAY DEVICES AND USE THEREOF

BACKGROUND OF THE INVENTION

1. Field of the Invention

This invention relates broadly to immunoassay devices and the methods for their use. More particularly, this invention relates to chromatographic quick test strips for detection of a ligand in a body fluid.

2. State of the Art

Many types of ligand-receptor assays have been used to detect the presence of various substances, often generally called ligands, in body fluids such as blood, urine, or saliva. These assays involve antigen antibody reactions, synthetic conjugates comprising radioactive, enzymatic, fluorescent, or visually observable polystyrene or metal sol tags, and specially designed reactor chambers. In all these assays, there is a receptor, e.g., an antibody, which is specific for the selected ligand or antigen, and a means for detecting the presence, and in some cases the amount, of the ligand-receptor reaction product. Some tests are designed to make a quantitative determination, but in many circumstances all that is required is a positive/negative qualitative indication. Examples of such qualitative assays include blood typing, most types of urinalysis, pregnancy tests, and AIDS tests. For these tests, a visually observable indicator such as the presence of agglutination or a color change is preferred.

Even the qualitative assays must be very sensitive because of the often small concentration of the ligand of interest in the test fluid. False positives can also be troublesome, particularly with agglutination and other rapid detection methods such as dipstick and color change tests. Because of these problems, so-called "sandwich" assays and other sensitive detection mechanisms which use metal sols or other types of colored particles have been developed.

In the "sandwich" method, a target analyte such as an antigen is "sandwiched" between a labeled antibody and an antibody immobilized onto a solid support. The assay is read by observing the presence and/or amount of bound antigen-labeled antibody complex. In the competition immunoassay method, antibody bound to a solid surface is contacted with a sample containing an unknown quantity of antigen analyte and with labeled antigen of the same type. The amount of labeled antigen bound on the solid surface is then determined to provide an indirect measure of the amount of antigen analyte in the sample.

Because these and other methods can detect both antibodies and antigens, they are generally referred to as immunochemical ligand-receptor assays or simply immunoassays.

Solid phase immunoassay devices, whether sandwich or competition type, provide sensitive detection of an analyte in a biological fluid sample such as blood, urine, or saliva. Solid phase immunoassay devices incorporate a solid support to which one member of a ligand-receptor pair, usually an antibody, antigen, or hapten, is bound. Common early forms of solid supports were plates, tubes, or beads of polystyrene which were well known from the fields of radioimmunoassay and enzyme immunoassay. In the last decade, a number of porous materials such as nylon, nitrocellulose, cellulose acetate, glass fibers, and other porous polymers have been employed as solid supports.

A number of self-contained immunoassay kits using porous materials as solid phase carriers of immunochemical components such as antigens, haptens, or antibodies have been described. These kits are usually dipstick, flow-through, or migratory in design.

In the more common forms of dipstick assays, as typified by home pregnancy and ovulation detection kits, immunochemical components such as antibodies are bound to a solid phase. The assay device is "dipped" for incubation into a sample suspected of containing unknown antigen analyte. Enzyme-labeled antibody is then added, either simultaneously or after an incubation period. The device is then washed and inserted into a second solution containing a substrate for the enzyme. The enzyme-label, if present, interacts with the substrate, causing the formation of colored products which either deposit as a precipitate onto the solid phase or produce a visible color change in the substrate solution.

Flow-through type immunoassay devices were designed to obviate the need for extensive incubation and cumbersome washing steps associated with dipstick assays. Valkirs et al., U.S. Pat. No. 4,632,901, disclose a device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample.

Korom et al., EP-A 0 299 359, discloses a variation in the flow-through device in which the labeled antibody is incorporated into a membrane which acts as a reagent delivery system.

The requirement of multiple addition and washing steps with dipstick and flow-through type immunoassay devices increases the likelihood that minimally trained personnel and home users will obtain erroneous assay results.

In migration type assays, a membrane is impregnated with the reagents needed to perform the assay. An analyte detection zone is provided in which labeled analyte is bound and assay indicia is read. See, for example, Tom et al., U.S. Pat. No. 4,366,241, and Zuk, et al. U.S. Pat. No. 4,596,275. The sensitivity of migration type assays is frequently reduced, however, by the presence or formation in the sample of undesirable solid components which block the passage of labeled analyte to the detection zone. Assay sensitivity also declines when migration assay devices are flooded with too much liquid sample.

Migration assay devices usually incorporate within them reagents which have been attached to colored labels (i.e., conjugates), thereby permitting visible detection of the assay results without addition of further substances. See, for example, Bernstein, U.S. Pat. No. 4,770,853. Among such labels are gold sol particles such as those described by Leuvering in U.S. Pat. No. 4,313,734, dye sol particles such as described in U.S. Pat. No. 4,373,932 by Gribnau et al., dyed latex such as described by May et al., WO 88/08534, and dyes encapsulated in liposomes by Campbell et al., U.S. Pat. No. 4,703,017. These colored labels are generally limited in terms of the immobilization methods which are suitable. Moreover, they require a relatively large amount of ligand molecule and can involve expensive reagents, thereby adding to the cost. Thus, there still remains a need for extremely reliable but inexpensive rapid detection devices. There also still remains a need for a highly sensitive assay which can utilize a small sample volume while providing accurate results.

SUMMARY OF THE INVENTION

It is therefore an object of the invention to provide a rapid detection immunoassay device.

It is another object of the invention to provide immunoassay devices which are simple to use and provide accurate results.

It is a further object of the invention to provide immunoassay devices which do not require migration of analytes.

It is also an object of the invention to provide rapid detection immunoassay devices which are simple in construction.

It is an additional object of the invention to provide immunoassay devices which can use either a dry or liquid conjugate system.

Another object of the invention is to provide a highly sensitive immunoassay device which provides accurate results while using small sample volumes.

A further object of the invention is to provide highly sensitive immunoassay devices which are useful with different types of body fluids.

In accord with these objects, which will be discussed in detail below, both dry and liquid conjugate immunoassay device systems are provided. The systems of the invention include test cells with a housing, a first opening in the housing for receiving a buffer solution (in the case of a dry conjugate system) or a conjugate solution (in the case of a liquid conjugate system), a sorbent material defining a horizontal flow path in the housing, a test line or test site with immobilized antigens or antibodies or other ligand binding molecules such as aptamers, nucleic acids, etc., a second opening in the housing directly above the test line or test site for receiving a sample, and a filter located in or adjacently below the second opening and above the test line or test site. The systems of the invention preferably also include a control line or site.

According to one embodiment of the invention, the filter is located in the second opening and removable from the housing once the sample has been applied so that the test line may be viewed.

According to another embodiment of the invention, the filter is located in the housing and is not removable, and a test line viewing window is provided in the housing on the opposite side of the filter. If desired, the viewing window may be sized so that the control line may also be viewed therethrough. Alternatively, a second viewing window may be provided for the control line.

In the dry conjugate system of the invention, a dry conjugate is provided between the first opening and the test site. The conjugate is supported on or within the sorbent material such that when a buffer is added in the first opening, the sorbent material wicks the buffer to the conjugate which is then carried by the buffer to the test site. In the liquid conjugate system of the invention, a buffer-conjugate liquid subsystem is provided and applied to the first opening. The sorbent material then wicks the buffer-conjugate subsystem to the test site.

According to one method of the invention, a system is provided which includes a test cell with a housing, a first opening in the housing, a sorbent material defining a horizontal flow path in the housing, the sorbent material optionally supporting an antibody or antigen conjugate, a test line or test site with immobilized antigens or antibodies or other ligand binding molecules such as aptamers, nucleic acids, etc., a second opening in the housing directly above the test line, a filter located in or adjacently below the second opening and above the test line or test site, and optionally a control line or site. A sample of interest is provided in the second opening. After a desired amount of time, a liquid such as a buffer solution is added to the first opening. If the sorbent material is supporting a conjugate (i.e., in a dry conjugate system), the liquid is preferably simply a buffer solution. If the sorbent material is not supporting a conjugate (i.e., in a liquid conjugate system), the liquid is preferably a buffer-conjugate liquid subsystem. In any event, after sufficient time to permit the conjugate to migrate to the test site (and control site if provided), the test site (and control site if provided) is inspected in order to determine whether the sample is "positive" or not.

Where the test cell includes a removable filter, the filter is removed prior to inspecting the test site and control site. Where the test cell includes a non-removable filter, the test cell is turned over and inspection of the test site and the control site is made through a window(s) in the test cell.

It will be appreciated that the system of the invention can be used in conjunction with different types of samples such as blood, urine, saliva, and feces, and can be used to test for the presence of any ligand. The type of filter located above the test site can be changed depending upon the type of sample to be provided and the type of ligand involved. Where blood, saliva or feces is to be provided, the blood, saliva or feces may be diluted or mixed with buffer prior to being added through the second hole.

The test cell of the invention has numerous advantages over the prior art. First, the test cell of the invention has a higher sensitivity than a conventional strip test because in the test cell of the invention the analyte in the sample does not need to horizontally migrate through a sorbent material to the test site but can directly bind (after filtering) to the immobilized specific binder in the test line. Thus, only a small volume of sample will be required. Second, because there is no horizontal migration of the analyte, there is less risk for non-specific binding because the analyte does not need to migrate together with the conjugate across the membrane to the test site. A third advantage of the invention is that the assay time is reduced significantly when the sample involved is blood, feces, or saliva, as those samples tend to migrate very slowly in the conventional chromatographic strip tests. Fourth, the test cell of the invention overcomes aggregation/agglutination problems between the conjugate and the analyte in the sample which is a significant problem in traditional chromatographic immunoassay for relatively large analytes such as bacteria. In particular, in traditional chromatographic immunoassays, the complex between bacteria and conjugated antibody has difficulty migrating to the test line and tends to remain in the bottom of test strip or in the pad. In this invention there is no complex binding between analyte and the conjugate until the sample reaches the test site, as the analyte is applied through the filter directly to the test site and conjugate migrates by itself. As a result, the system of the invention is extremely sensitive and specific.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
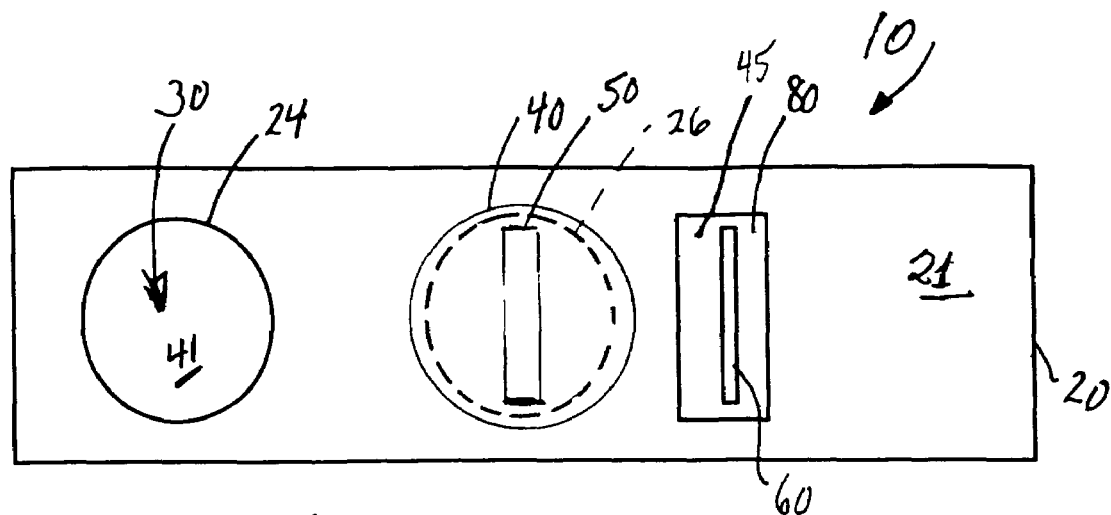
FIG. 1 is a top schematic view of a dry conjugate system according to a first embodiment of the invention.
Figure 2:
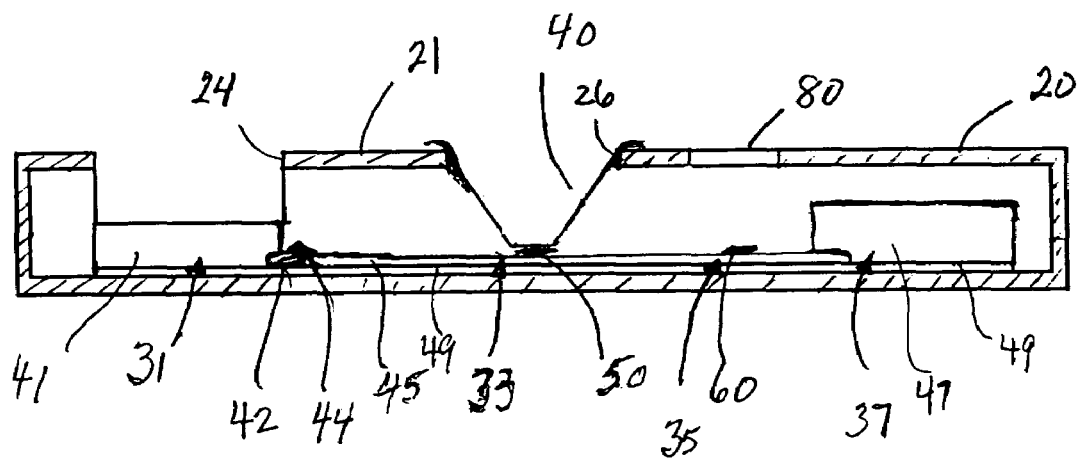
FIG. 2 is a longitudinal sectional view of the dry conjugate system of FIG. 1.

Turning now to FIGS. 1 and 2, an immunoassay device test cell 10 is provided and includes a housing 20 having a top wall 21 defining first and second holes 24, 26, a sorbent or bibulous material 30 defining a horizontal flow path in the housing, and a filter 40 located in the second hole 26. The sorbent material includes at least two and preferably three or four zones and may be made from a plurality of materials. A first zone 31 (sometimes called a filter zone) is located at the first hole 24 and extends to a second zone 33 (sometimes called a test zone) which is located under the second hole 26. The first zone 31 preferably includes a filter 41, a pad 42 on or in which a conjugate 44 having desired antigens or antibodies with attached colored markers is deposited and immobilized, and a thin membrane 45 typically made from nitrocellulose. The first zone 31 is adapted to receive a buffer solution, to cause the buffer solution to contact the conjugate 44, thereby mobilizing the conjugate, and to wick the conjugate-carrying buffer solution to the second zone 33. The second (test) zone 33 is preferably printed with a test line 50 having immobilized antigens or antibodies (depending on whether the test cell is designed to test for the presence of antibodies or antigens) on the membrane 45 as is well known in the art. An optional third zone 35 (sometimes called a control zone) may also be printed with a control line 60 typically containing antibodies to the conjugate antigens (or in some cases antibodies which will bind to conjugate antibodies, or even antigens which will bind to conjugate antibodies) as is well known in the art. Where the third zone 35 is provided, a window 80 of clear plastic is preferably provided in the housing 20 above the control line 60. If desired, an optional fourth zone 37 (sometimes called a reservoir zone) may be provided as a wicking reservoir as is also well known in the art. The fourth zone 37 includes a relatively thicker absorbent paper 47. Preferably underlying all four zones is a thin plastic film 49 having an adhesive which keeps the sorbent materials in place.

As seen best in FIG. 2, the filter 40 is located directly above the test line 50 in the second zone 33. The filter is preferably an absorbent pad/filter which is coated with plastic except at its bottom area, and which is removably assembled through the second hole 26. In a preferred embodiment of the invention, the filter has a wide circular mouth (coated with plastic) into which the test sample is provided, and is shaped as a funnel which narrows down in one axis only so that a cross-section through the non-coated bottom of the funnel is essentially rectangular in shape and is substantially the same size as the test line 50.

The immunoassay of FIGS. 1 and 2 is preferably utilized as follows. First, a sample (not shown) possibly containing antibodies (or antigens) is provided to the filter 40 via the second opening or hole 26. Because the filter is coated with plastic on its top portion, the sample is directed to the bottom rectangularly-shaped portion where it is filtered. After a desired amount of time, by which time the antibodies (or antigens) in the sample (if present) will have had an opportunity to bind to the antigens (or antibodies) immobilized at the test line 50, a preferably measured amount of liquid such as a buffer solution (not shown) is added to the first opening 24. After another period of time, sufficient to permit the conjugate to migrate to the test site 50 (and control site 60 if provided), the filter 40 is removed, and the test site 50 (and control site 60 if provided) is inspected through hole 26 (and window 80) in order to determine whether the sample is "positive" or not. Typically, a "positive" test indicating the presence of the antibody (or antigen) in the sample is obtained when both the test site 50 and the control site 60 show lines of color. A "negative" test indicating the lack of the presence of the antibody (or antigen) in the sample is obtained when only the control site 60 shows a line of color.

The method of the invention may be expedited by providing the housing with numbering and/or lettering to indicate that hole 26 is for receiving the sample and is to be used first and that hole 24 is for receiving the buffer solution and is to be used second.

Those skilled in the art will appreciate that the immunoassay 10 functions as follows. Because the test line 50 is provided with antigens (or antibodies) immobilized on a membrane, if the test sample contains antibodies to the antigens (or antigens to the antibodies), the antibodies (or antigens) will bind themselves to the antigens (or antibodies) at the test line. Thereafter, when the conjugate 44 containing an antigen for the antibody (or antibody for the antigen) coupled to a colored marker is caused to migrate to the test line, if the test sample contains the antibodies (or antigens) which are now held at the test line 50, the antigen (or antibody) of the conjugate will bind itself to the antibodies (or antigens) and the colored marker will cause a colored line to appear at the test site 50. If the test sample does not contain antibodies (or antigens), the conjugate will not have the antibodies (antigens) to bind to at the test line 50, and no colored line will appear at the test site 50. On the other hand, because the control line 60 is provided with antibodies (or antigens), the antigens (or antibodies) of the conjugate will always bind to the antibodies (or antigens) in the control line 60, thereby causing a colored line to appear at the control site 60 if the conjugate reaches the control site 60. Thus, if sufficient buffer solution is provided to the test cell, a colored line should always appear at the control site 60, thereby providing a control for the test.

Figure 3:
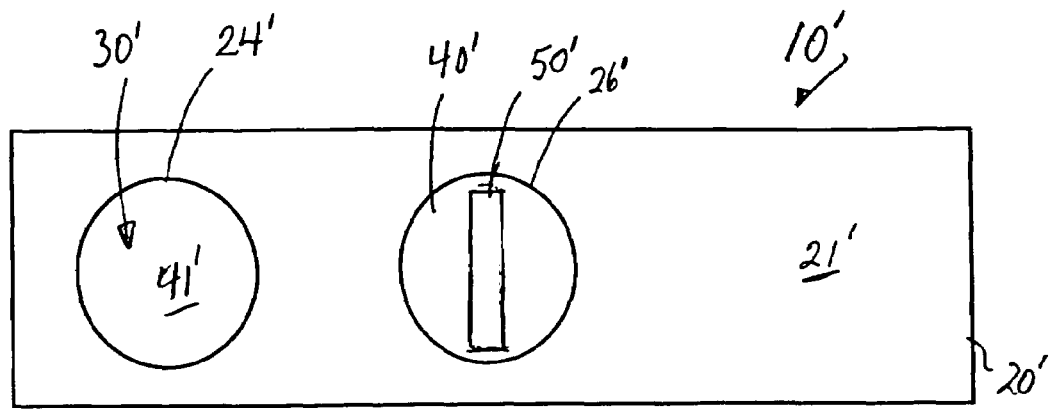
FIG. 3 is a top schematic view of a second embodiment of the dry conjugate system according to the invention.
Figure 4:
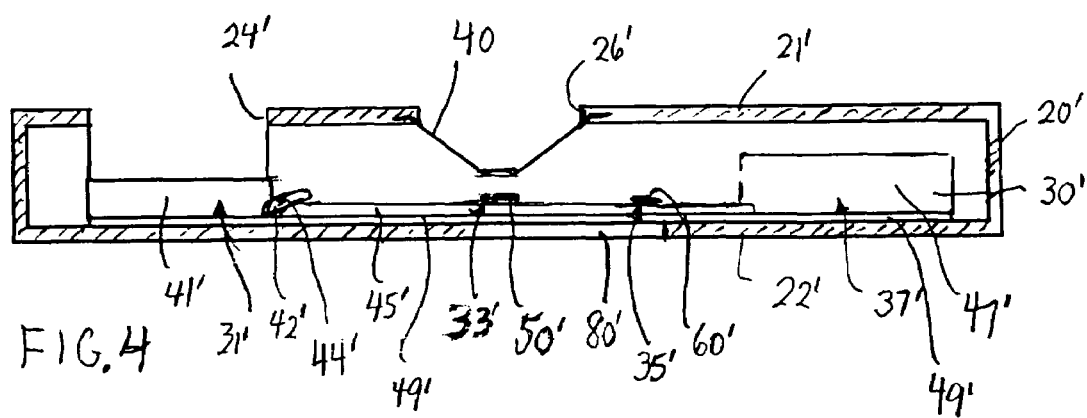
FIG. 4 is a longitudinal sectional view of the second embodiment of FIG. 3.

Turning now to FIGS. 3 and 4, a second embodiment of the immunoassay device is shown with a test cell 10' (slightly modified relative to test cell 10 of FIGS. 1-2) provided which includes a housing 20' having a top wall 21' defining first and second holes 24', 26', a bottom wall 22' defining a window 80', a sorbent material 30' defining a horizontal flow path in the housing, and a filter 40' located in test housing adjacently below the second hole 26'. The sorbent material includes at least two and preferably three or four zones and may be made from a plurality of materials. A first zone 31' (sometimes called a filter zone) is located at the first hole 24' and extends to a second zone 33' (sometimes called a test zone) which is located under the second hole 26'. The first zone 31' preferably includes a filter 41', a pad 42' on or in which a conjugate 44' having desired antigens or antibodies with attached colored markers is deposited and immobilized, and a membrane 45'. The first zone 31' is adapted to receive a buffer solution, to cause the buffer solution to contact the conjugate 44', thereby mobilizing the conjugate, and to wick the conjugate-carrying buffer solution to the second zone 33'. The second (test) zone 33' is preferably printed with a test line 50' having immobilized antigens or antibodies (depending on whether the test cell is designed to test for the presence of antibodies or antigens) on the membrane 45' as is well known in the art.

An optional third zone 35' (sometimes called a control zone) may also be printed with a control line 60' typically containing antibodies to the conjugate antigens (or in some cases antibodies which will bind to conjugate antibodies) as is well known in the art. If desired, an optional fourth zone 37' (sometimes called a reservoir zone) may be provided as a wicking reservoir as is also well known in the art. The fourth zone 37' includes a relatively thicker absorbent paper 47'. Preferably underlying all four zones is a thin plastic film 49' having an adhesive which keeps the sorbent materials in place.

As is seen in FIGS. 3 and 4, the filter 40' is located directly above the test line in the second zone 33'. The filter is preferably an absorbent pad/filter which is coated with plastic except at its bottom area and is fixed in the housing 20' directly under the second hole 26'. If desired, the housing may be provided with a stepped surface in order to receive and hold the filter. As with the embodiment of FIGS. 1-2, the preferred filter 40' has a wide circular mouth (plastic coated) into which the test sample is provided, and is shaped as a funnel which narrows down in one axis only so that a cross-section through the bottom of the funnel is essentially rectangular in shape and is substantially the same size as the test line 50'.

As previously mentioned, the bottom wall 22' of the housing 20' defines a window 80'. The window is preferably a clear plastic and is located on the side of the housing which is opposite the filter 40' at the location of the test site 50'. In the preferred embodiment, the window 80' also extends to the location of the control site 60'. Alternatively, a separate window on the bottom or the top of the housing can be provided at the control site 60'.

The immunoassay of FIGS. 3 and 4 is preferably utilized as follows—(for purposes of clarity, the use of the immunoassay will be described with reference to an assay for identifying a sample containing an antibody, although those skilled in the art will appreciate how to use a similar immunoassay for identifying a sample containing an antigen). First, a sample (not shown) possibly containing antibodies is provided to the filter 40' via the second opening or hole 26'. Because the filter is coated with plastic on its top portion, the sample is directed to the bottom rectangularly-shaped portion where it is filtered. After a desired amount of time, by which time the antibodies in the filtered sample (if present) will have had an opportunity to bind to the antigens immobilized at the test line 50', a preferably measured amount of liquid such as a buffer solution (not shown) is added to the first opening 24'. After another period of time, sufficient to permit the conjugate to migrate to the test site 50' (and control site 60' if provided), the test site 50' (and control site 60' if provided) is inspected through the window 80' in the back side of the cell 10' in order to determine whether the sample is "positive" or not. The inspection may be done by turning the housing 20' over and visually inspecting the test site. Typically, a "positive" test indicating the presence of the antibody in the sample is obtained when both the test site 50' and the control site 60' show lines of color. A "negative" test indicating the lack of the presence of the antibody in the sample is obtained when only the control site 60' shows a line of color.

Those skilled in the art will appreciate that the immunoassay test cell 10' of FIGS. 3 and 4 functions substantially the same as the test cell 10 of FIGS. 1 and 2.

Figure 5:
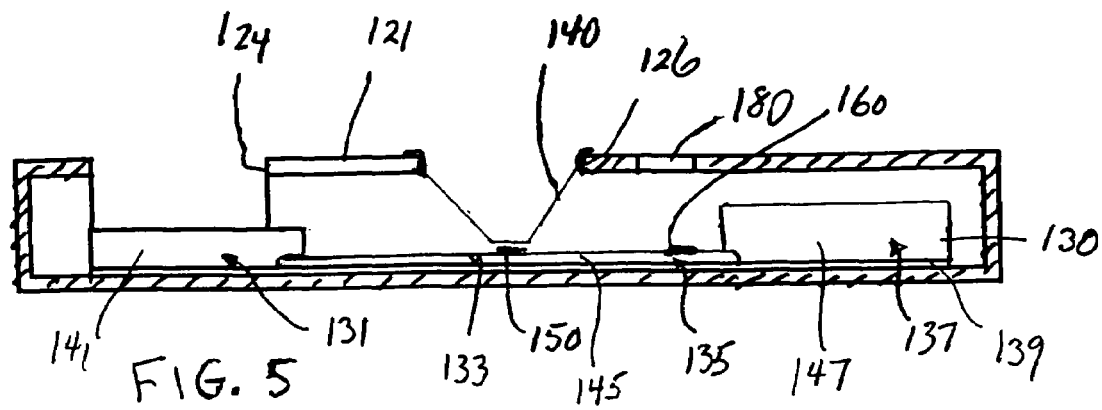
FIG. 5 is a longitudinal sectional view of a liquid conjugate system according to the invention and similar to the system of FIGS. 1 and 2.

Turning now to FIG. 5, an immunoassay device test cell 110 (alternate to the first embodiment) is provided and includes a housing 120 having a top wall 121 defining first and second holes 124, 126, a sorbent material 130 defining a horizontal flow path in the housing, and a filter 140 located in the second hole 126. The sorbent material includes at least two and preferably three or four zones and may be made from a plurality of materials. A first zone 131 (sometimes called a filter zone) is located at the first hole 124 and extends to a second zone 133 (sometimes called a test zone) which is located under the second hole 126. The first zone 131 preferably includes a filter 141 and a thin membrane 145 typically made from nitrocellulose. The first zone 131 is adapted to receive a buffer solution and to wick the conjugate-carrying buffer solution to the second zone 133. The second (test) zone 133 is preferably printed with a test line 150 having immobilized antigens or antibodies (depending on whether the test cell is designed to test for the presence of antibodies or antigens) on the membrane 145 as is well known in the art. An optional third zone 135 (sometimes called a control zone) may also be printed with a control line 160 typically containing antibodies to the conjugate antigens as is well known in the art. Where the third zone 135 is provided, a window 180 of clear plastic is preferably provided in the housing 120 above the control line 160. If desired, an optional fourth zone 37 (sometimes called a reservoir zone) may be provided as a wicking reservoir as is also well known in the art. The fourth zone 37 includes a relatively thicker absorbent paper 147. Preferably underlying all four zones is a thin plastic film 149 having an adhesive which keeps the sorbent materials in place.

As seen in FIG. 5, the filter 140 is located directly above the test line in the second zone 133. The filter is preferably an absorbent pad/filter which is coated with plastic except at its bottom portion and is removably assembled through the second hole 126. In a preferred embodiment of the invention, the filter has a wide circular mouth (plastic coated) into which the test sample is provided, and is shaped as a funnel which narrows down in one axis only so that a cross-section through the bottom of the funnel is essentially rectangular in shape and is substantially the same size as the test line 150.

The embodiment of FIG. 5 differs from the embodiment of FIGS. 1 and 2 only in that a dry conjugate is not provided in the test cell.

The immunoassay of FIG. 5 is preferably utilized as follows (again being described with reference to an assay for identifying a sample containing an antibody, although those skilled in the art will appreciate how to use a similar immunoassay for identifying a sample containing an antigen). First, a sample (not shown) possibly containing antibodies is provided to the filter 140 via the second opening or hole 126. Because the filter is coated with plastic on its top portion, the sample is directed to the bottom rectangularly-shaped portion where it is filtered. After a desired amount of time, by which time the antibodies will have had an opportunity to bind to the antigens immobilized at the test line 150, a preferably measured amount of liquid subsystem (not shown) including a buffer solution and a conjugated antigen-marker is added to the first opening 124. After another period of time, sufficient to permit the subsystem to migrate to the test site 150 (and control site 160 if provided), the filter 140 is removed, and the test site 150 (and control site 160 if provided) is inspected through hole 126 (and window 180) in order to determine whether the sample is "positive" or not. Typically, a "positive" test indicating the presence of the antibody in the sample is obtained when both the test site 150 and the control site 160 show lines of color. A "negative" test indicating the lack of the presence of the antibody in the sample is obtained when only the control site 160 shows a line of color.

Those skilled in the art will appreciate that the immunoassay 110 functions as follows. Because the test line 150 is provided with antigens immobilized on a membrane, if the test sample contains antibodies to the antigens, the antibodies will bind themselves to the antigens at the test line. Thereafter, when the conjugate subsystem is added to the horizontal flow path and migrates to the test line, if the test sample contains the antibodies which are now held at the test line 150, the antigen of the conjugate subsystem will bind itself to the antibodies and the colored marker will cause a colored line to appear at the test site 150. If the test sample does not contain antibodies, the conjugate will not have the antibodies to bind to at the test line 150, and no colored line will appear at the test site 150. On the other hand, because the control line 160 is provided with antibodies, the antigen of the conjugate will always bind to the antibodies in the control line 160, thereby causing a colored line to appear at the control site 160 if the conjugate reaches the control site 160. Thus, if a sufficient amount of the conjugate subsystem is provided to the test cell, a colored line should always appear at the control site 160, thereby providing a control for the test.

Figure 6:
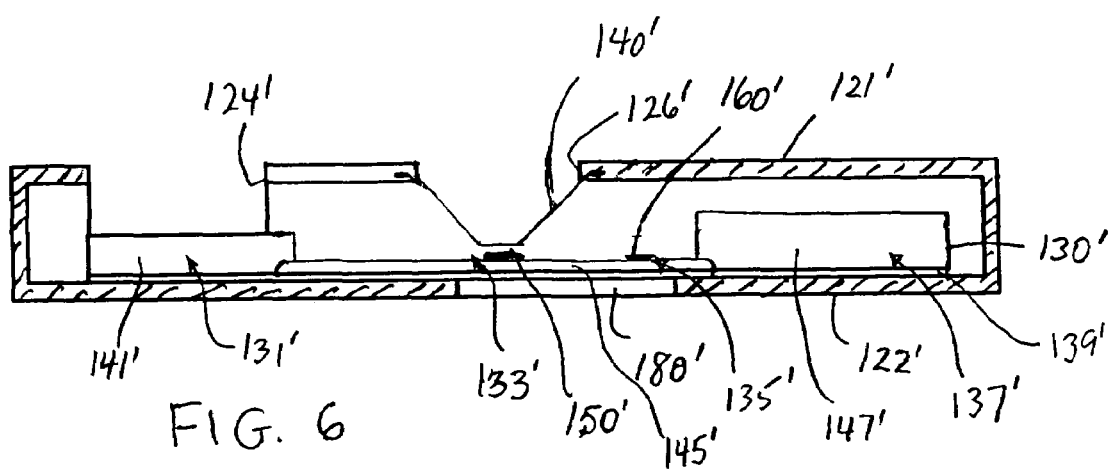
FIG. 6 is a longitudinal sectional view of a liquid conjugate system according to the invention and similar to the system of FIGS. 3 and 4.

Turning now to FIG. 6, an alternative second embodiment of the immunoassay device test cell 110' (slightly modified relative to test cell 10' of FIGS. 3-4) is provided and includes a housing 120' defining first and second holes 124', 126' and a window 180', a sorbent material 130' defining a horizontal flow path in the housing, and a filter 140' located in test housing adjacently below the second hole 126'. The sorbent material includes at least two and preferably three or four zones and may be made from a plurality of materials. A first zone 131' (sometimes called a filter zone) is located at the first hole 124' and extends to a second zone 133' (sometimes called a test zone) which is located under the second hole 126'. The first zone 31' preferably includes a filter 141' and a membrane 145'. The first zone 131' is adapted to receive a buffer-conjugate subsystem and to wick the buffer-conjugate subsystem to the second zone 133'. The second (test) zone 133' is preferably printed with a test line 150' having immobilized antigens or antibodies (depending on whether the test cell is designed to test for the presence of antibodies or antigens) on the membrane 145' as is well known in the art. An optional third zone 135' (sometimes called a control zone) may also be printed with a control line 160' typically containing antibodies to the conjugate antigens (or in some cases antibodies which will bind to conjugate antibodies) as is well known in the art. If desired, an optional fourth zone 137' (sometimes called a reservoir zone) may be provided as a wicking reservoir as is also well known in the art. The fourth zone 137' includes a relatively thicker absorbent paper 147'. Preferably underlying all four zones is a thin plastic film 149' having an adhesive which keeps the sorbent materials in place.

The filter 140' is located directly above the test line in the second zone 133'. The filter is preferably an absorbent pad/filter which is coated with plastic except at a bottom portion and which is fixed in the housing 120' directly under the second hole 126'. If desired, the housing may be provided with a stepped surface in order to receive and hold the filter. The preferred filter 140' has a wide circular mouth (plastic coated) into which the test sample is provided, and is shaped as a funnel which narrows down in one axis only so that a cross-section through the bottom of the funnel is essentially rectangular in shape and is substantially the same size as the test line 150'.

As previously mentioned, the housing 120' defines a window 180'. The window is preferably a clear plastic and is located on the side of the housing which is opposite the filter 140' at the location of the test site 150'. In the preferred embodiment, the window 180' also extends to the location of the control site 160'. Alternatively, a separate window on the bottom or the top of the housing can be provided at the control site 160'.

The embodiment of FIG. 6 differs from the embodiment of FIGS. 3 and 4 only in that a dry conjugate is not provided in the test cell.

The immunoassay of FIG. 6 is preferably utilized as follows—(again being described with reference to an assay for identifying a sample containing an antibody, although those skilled in the art will appreciate how to use a similar immunoassay for identifying a sample containing an antigen). First, a sample (not shown) possibly containing antibodies is provided to the filter 140' via the second opening or hole 126'. Because the filter is coated with plastic on its top portion, the sample is directed to the bottom rectangularly-shaped portion where it is filtered. After a desired amount of time, by which time the antibodies will have had an opportunity to bind to the antigens immobilized at the test line 150', a preferably measured amount of liquid such as a buffer solution—conjugate subsystem (not shown) is added to the first opening 124'. After another period of time, sufficient to permit the conjugate to migrate to the test site 150' (and control site 160' if provided), the test site 150' (and control site 60' if provided) is inspected through the window 180' in the back side of the cell 110' in order to determine whether the sample is "positive" or not. Typically, a "positive" test indicating the presence of the antibody in the sample is obtained when both the test site 150' and the control site 160' show lines of color. A "negative" test indicating the lack of the presence of the antibody in the sample is obtained when only the control site 160' shows a line of color.

Those skilled in the art will appreciate that the immunoassay test cell 110' of FIG. 6 functions substantially the same as the test cell 110 of FIG. 5.

It will be appreciated by those skilled in the art that the embodiments of the invention may be realized using many different materials. For example, the sorbent material(s), which typically include a very thin, inert film, strip, sheet, or membrane may be formed from nitrocellulose, filter paper, silica, or from, e.g., microporous or microgranular woven or non-woven fabrics, or combinations thereof. Many types of suitable materials and combinations thereof are described in U.S. Pat. No. 4,960,691 to Gordon et al. and U.S. Pat. No. 4,956,275 to Zuk et al. which are both hereby incorporated by reference in their entireties. Often, the nitrocellulose or other sorbent materials will be provided with a thin non-porous inert plastic backing.

In a similar vein, it will be appreciated that the sorbent material can be shaped in any of many manners and take any of many dimensions as is known in the art. Thus, in order to help expedite wicking, the sorbent material can be key-shaped with the strip having smaller width at the first hole which receives the buffer solution and at the test site and control site, and a wider width at a reservoir (fourth) zone. Such an arrangement is shown in U.S. Pat. No. 5,989,921 to Charlton et al., which is hereby incorporated by reference in its entirety herein. In any event, generally, the test strip will be substantially greater in length than in width, and substantially greater in width than in thickness. Indeed, in at least certain embodiments of the present invention, the strip at the test zone should be paper-thin (e.g., 0.1 mm thick) and sufficiently translucent such that the test and control lines can easily be seen through the test strip.

Further, the housing and the sorbent material can be integrated in an open lateral flow platform where injection molded polymer is provided with micro-pillars which enable exact control over flow by varying the height, diameter, shape and/or distance between the pillars. Such a platform essentially uses the same material for the housing and the sorbent wicking material and is sold by Amic AB of Uppsala, Sweden. See, e.g., www.amic.se. Since the injection molded polymer may be generally transparent, the entire housing may be considered the "window" through which the test and control lines/sites may be viewed.

It will also be appreciated that depending upon the type of test being constructed (e.g., pregnancy, HIV, tuberculosis, prion, encephalitis, urine-analysis/drug, other bacteria or viruses, etc.), the antibody (or antigen) of interest will be different, and therefore the antigen (or antibody) used in the test strip will need to be tailored accordingly. Likewise, the antigen or antibody of the conjugate will need to be tailored accordingly. In some cases (such as HIV), the identical antigen may be utilized in the test strip as in the conjugate, as the binding site of the HIV antibody will bind with the HIV antigen at the test site and still provide additional binding sites for binding to the antigen-conjugate, while in other cases, different antigens might be required. Similarly, it will be appreciated that depending upon the type of test being constructed, the control site, where provided, will need to be tailored accordingly. Thus, for example, in an HIV antibody detection test, where the ligand being identified in the test zone will be the HIV 1 and/or HIV2 antibodies, the antigen in the test zone can be a mixture of HIV 1 and HIV 2 peptides and/or recombinant antigens. The conjugate can be a colored latex or colloidal gold conjugated to protein A/G, anti-human IgG/IgM, peptides or recombinant antigens.

It will also be appreciated by those skilled in the art that the marker of the conjugate may take many forms including different types of metal sols, a colored latex, any of various enzymes, etc. While the preferred embodiment of the invention provides a detection signal readily visible to the unaided eye, it will be appreciated that the invention encompasses other markers which can be detectible by ultraviolet radiation or other techniques such a fluoroscopy. Thus, it will be appreciated that a system employing the test cells of the invention which are read from the reverse side of the housing and an automatic reader such as a fluoroscopic or digital reader can be provided.

It is believed that the immunoassay test strip devices of the invention have higher sensitivity than the conventional test strips. Many immunochromatographic assays require a small volume of sample, and it is critical that the analyte in the sample bind efficiently to the conjugate at the sample site. It is known that in some instances the buffer will wash away the conjugate before the analyte has enough time to bind to the binder on the conjugate. This will create low sensitivity to the assay and false negative results will be observed resulting in health risks. The immunoassay test strips of the present invention overcomes these problems because they do not require horizontal migration of the sample. Thus, only a small volume of sample is required, and the sample will bind to the test site in advance of the provision of the conjugate and buffer.

The immunoassay test strip devices of the invention are also believed to have a higher specificity than the devices of the prior art because the analyte in the sample reacts immediately with specific binder in test site without any migration in the membrane, whereas in the prior art there is higher risk for non-specific binding when the analyte migrates together with conjugate across the membrane to the test site.

It is further believed that the immunoassay test strip devices of the invention provide decreased assay times relative to the devices of the prior art. In particular, it is known that blood, feces or saliva will migrate very slowly in the conventional chromatographic strip tests. However, in the immunoassay assay test strip devices of the invention, no migration is required, and therefore the assay time can be very fast relative to the prior art.

Further yet, it is believed that the migration of conjugated particles in the absence of the sample provides a more uniform and consistent migration, resulting in an improvement of background clearance.

Another advantage of the immunoassay test strip devices of the invention is that they overcome aggregation/agglutination problems between the conjugate and analyte in the sample which is a major problem for large analytes (such as bacteria) in traditional chromatographic immunoassays. In the prior art, the large complex between bacteria and conjugated antibodies has difficulty in migrating to the test line. As a result, the complex tends to remain in the bottom of test strip or in the pad. With the present invention, the bacteria in the sample are applied after filtering directly to the test site, and immobilized there, while the conjugate is free to migrate without the sample to the test site. When the conjugate reaches the test site, bacteria already captured by the immobilized antibody in the test site will bind to the conjugate. Thus, the system of the present invention is extremely sensitive and specific.

There have been described and illustrated herein several embodiments of immunoassays and methods of their use. While particular embodiments of the invention have been described, it is not intended that the invention be limited thereto, as it is intended that the invention be as broad in scope as the art will allow and that the specification be read likewise. Thus, while the specification discusses ligand binding using antigen/antibody reactions, other ligand binding mechanisms such as aptamer binding, nucleic acid binding, enzymatic binding, etc. may also be used. Also, while the test cells are described as having a single line for testing for a single ligand, it will be appreciated that multiple lines may be utilized for testing for more than one ligand. In such a case, a single housing may be utilized with a single hole for the sample, or alternatively, multiple holes could be utilized if desired. Further, while the test cells are described as having a hole in the top wall of a housing for buffer-solution or for a buffer-conjugate subsystem, it will be appreciated that the hole for the buffer solution could be provided in the end wall or side wall of the housing. Similarly, while the sorbent material was described as preferably including a thin plastic backing, it will be appreciated that the plastic backing could be provided only at certain locations or not be provided at all. Where only partial backings or no backings are provided, the test and control sites can be located on either or both sides of the sorbent material. Further yet, while a test strip and control strip are shown is being rectangular in configuration, it will be appreciated that the test and control sites can be configured differently such as in circles, squares, ovals, etc. In fact, the test site and control site can be configured differently from each other. It will therefore be appreciated by those skilled in the art that yet other modifications could be made to the provided invention without deviating from its spirit and scope as claimed.

What is claimed is:

1. A test device for determining the presence of a ligand in a liquid sample, comprising:
   a) a housing defining a first opening for receiving a solution and a second opening through which the liquid sample is deposited;
   b) a strip of sorbent material, said strip including a test site having an immobilized ligand-binding mechanism, said strip disposed within said housing defining a horizontal flow path for the solution from adjacent said first opening to said test site, said test site being directly below said second opening;
   c) a filter for filtering the sample, said filter located in or adjacently below the second opening and directly above said test site, wherein
   said housing has a top wall with said second opening defined in said top wall, and said housing has a bottom wall with a window defined in said bottom wall, said window located adjacent said test site and permitting viewing of said test site.

2. A test device according to claim 1, wherein:
   said strip supports a conjugate.

3. A test device according to claim 2, wherein:
   said ligand-binding mechanism is an antigen or antibody for said ligand, and said conjugate comprises an antigen or antibody for the ligand and a marker coupled to the antigen or antibody.

4. A test device according to claim 3, wherein:
   said marker is a colored marker viewable in the visible spectrum.

5. A test device according to claim 1, wherein:
   said strip includes a control site spaced from said test site in a direction opposite to said first opening, and said housing defines a second window for viewing said control site.

6. A test device according to claim 5, wherein:
   said second window is an extension of said window defined in said bottom wall.

7. A test device according to claim 1, wherein:
   said filter extends through said second hole and is removable from said test device.

8. A test device according to claim 1, wherein:
   said filter has a wide mouth and a narrow base.

9. A test device according to claim 8, wherein:
   said test site is rectangular and said narrow base of said filter defines a rectangular cross section.

10. A test device according to claim 9, wherein:
    said wide mouth of said filter is coated with plastic.

11. A test device according to claim 1, further comprising:
    said solution which comprises a buffer.

12. A test device according to claim 1, further comprising:
    said solution which comprises a subsystem of a buffer and a conjugate having an antigen or antibody for the ligand and a marker coupled to the antigen or antibody.

13. A test device according to claim 1, wherein:
    said test site having an immobilized ligand-binding mechanism has an HIV antigen or antibody.

14. A test device according to claim 1, wherein:
    said test site having an immobilized ligand-binding mechanism has one of antigens, antibodies, aptamers, nucleic acids, or enzymes for testing for pregnancy, tuberculosis, prion, or drugs.

15. A test device for determining the presence of a ligand in a liquid sample, comprising:
    a) a housing defining a first opening for receiving a solution and a second opening through which the liquid sample is deposited;
    b) a strip of sorbent material, said strip including a test site having an immobilized ligand-binding mechanism, said strip disposed within said housing defining a horizontal flow path for the solution from adjacent said first opening to said test site;
    c) a filter for filtering the liquid sample extending through said second hole directly above said test site, and having a wide mouth and a narrow base which defines a rectangular cross-section, said filter being removable from said test device.

16. A test device according to claim 15, wherein:
    said strip supports a conjugate, and
    said ligand-binding mechanism is an antigen or antibody for said ligand, and said conjugate comprises an antigen or antibody for the ligand and a marker coupled to the antigen or antibody.

17. A test device according to claim 15, wherein:
    said test site having an immobilized ligand-binding mechanism has an HIV antigen or antibody.

18. A test device according to claim 15, wherein:
    said test site having an immobilized ligand-binding mechanism has one of antigens, antibodies, aptamers, nucleic acids, or enzymes for testing for pregnancy, tuberculosis, prion, or drugs.

19. A test device according to claim 15, wherein:
    said housing has a top wall with said second opening defined in said top wall, and said housing has a bottom wall with a window defined in said bottom wall, said window located adjacent said test site and permitting viewing of said test site.

* * * * *